(12) United States Patent
Yamashita et al.

(10) Patent No.: US 7,485,852 B2
(45) Date of Patent: Feb. 3, 2009

(54) MASS ANALYSIS METHOD AND MASS ANALYSIS APPARATUS

(75) Inventors: Hiromichi Yamashita, Hitachinaka (JP); Akihiro Takeda, Hitachinaka (JP); Tomoyuki Kurosawa, Hitachi (JP); Kinya Kobayashi, Hitachi (JP)

(73) Assignee: Hitachi High-Technologies Corporation, Tokyo (JP)

( * ) Notice: Subject to any disclaimer, the term of this patent is extended or adjusted under 35 U.S.C. 154(b) by 449 days.

(21) Appl. No.: 11/442,113

(22) Filed: May 30, 2006

(65) Prior Publication Data
US 2006/0289736 A1    Dec. 28, 2006

(30) Foreign Application Priority Data
May 30, 2005    (JP)    ............................. 2005-156508

(51) Int. Cl.
B01D 59/44    (2006.01)
(52) U.S. Cl. .................. 250/282; 250/281; 250/286; 250/288; 422/68.1; 422/70; 702/23; 702/27
(58) Field of Classification Search ................ 250/281, 250/282, 286, 288; 422/68.1, 70; 702/23, 702/27
See application file for complete search history.

(56) References Cited

U.S. PATENT DOCUMENTS

| 6,147,348 | A * | 11/2000 | Quarmby et al. | ............ 250/292 |
| 6,745,134 | B2 * | 6/2004 | Kobayashi et al. | ............ 702/27 |
| 2004/0041091 | A1 * | 3/2004 | Bateman et al. | ............ 250/282 |
| 2004/0108452 | A1 * | 6/2004 | Graber et al. | ............ 250/281 |
| 2004/0111228 | A1 * | 6/2004 | Kobayashi et al. | ............ 702/81 |
| 2004/0169138 | A1 * | 9/2004 | Ootake et al. | ............ 250/281 |
| 2004/0222369 | A1 * | 11/2004 | Makarov et al. | ............ 250/281 |
| 2005/0063864 | A1 * | 3/2005 | Sano et al. | ............ 422/68.1 |
| 2005/0199804 | A1 * | 9/2005 | Hunt et al. | ............ 250/290 |

(Continued)

FOREIGN PATENT DOCUMENTS

JP    9-510780 A    10/1997

(Continued)

Primary Examiner—Jack I Berman
Assistant Examiner—Michael J Logie
(74) Attorney, Agent, or Firm—McDermott Will & Emery LLP

(57) ABSTRACT

The present invention achieves a mass analysis method that can identify protein or peptide with high speed and high sensitivity. A mass spectrum is obtained from a standard sample of healthy person, an ion is selected from the mass spectrum as a precursor ion, and a mass spectrum of the precursor ion is obtained [(a) to (d)]. A mass spectrum is obtained from a sample of interest to be measured of patient, an ion other than the precursor ion of the standard sample is selected from the mass spectrum as a precursor ion, and a mass spectrum of the precursor ion is obtained [(g) to (k)]. Identifications on peptide/protein specific to the standard sample and the sample to be measured, and common to both are conducted [(r) to (q)], and based on the results, comparative analysis on peptide/protein of the sample to be measured (t). Without regarding an ion derived from all components of the sample to be measured as precursor ion, MS/MS spectrum is obtained and identification on a plurality of components of the sample to be measured can be conducted for a short time and with high sensitivity.

12 Claims, 7 Drawing Sheets

U.S. PATENT DOCUMENTS

| | | |
|---|---|---|
| 2005/0258355 A1* | 11/2005 | Ogata et al. .................. 250/281 |
| 2006/0078960 A1* | 4/2006 | Hunter et al. .................. 435/25 |
| 2006/0284080 A1* | 12/2006 | Makarov et al. ............ 250/290 |

FOREIGN PATENT DOCUMENTS

| | | |
|---|---|---|
| JP | 2003-510008 A | 3/2003 |
| JP | 2003-315341 | 6/2003 |
| WO | WO 95/25281 | 9/1995 |
| WO | WO 00/12765 | 9/2000 |

\* cited by examiner

Fig. 4

CONDITIONS FOR PREPARATION OF PRECURSOR ION EXCLUSION LIST

ANALYSIS CONDITIONS ON THE MEASUREMENT DATA OF HEALTHY PERSON
MEASUREMENT DATA FILE
`C:¥Data¥Standard.dat`

| | | |
|---|---|---|
| THRESHOLD VALUE OF IONIC INTENSITY | 10 | % ▼ |
| RETENTION TIME RANGE (min) | 20 | 60 |
| RETENTION TIME ACCURACY (sec) | 10 | |
| MASS RANGE (Da) | 50 | 40000 |
| MASS ACCURACY (Da) | 1 | |

[MEASUREMENT DATA ANALYSIS EXECUTION] — 2 0

OBSERVED IONS IN MS$^1$ SPECTRA OF MEASUREMENT DATA
RETENTION TIME (min)

| APPEARANCE | DISAPPEARANCE | REPRESENTATIVE | MASS (M/Z) | CHARGE |
|---|---|---|---|---|
| 0.0 | 90.1 | 80.1 | 354.4 | 1 |
| 14.2 | 14.5 | 14.3 | 639.5 | 2 |
| 14.5 | 15.1 | 14.8 | 570.2 | 2 |
| 16.8 | 17.4 | 17.0 | 345.1 | 3 |

CONDITIONS FOR OUTPUTTING PRECURSOR ION EXCLUSION LIST

☑ MULTIPLY-CHARGED ION EXTENSION

RETENTION TIME TYPE    ◉ RANGE   ◎ REPRESENTATIVE VALUE

PRECURSOR ION EXCLUSION LIST FILE
`C:¥Data¥Standard.dat`

[PRECURSOR ION EXCLUSION LIST PREPARATION EXECUTION]

Fig. 5

| CONDITIONS FOR PRECURSOR ION COMPARATIVE ANALYSIS |
|---|
| CONDITIONS FOR MEASUREMENT DATA COMPARATIVE ANALYSIS <br> MEASUREMENT DATA FILE OF HEALTHY PERSON <br> `C:¥Data¥Standard.dat` <br> MEASUREMENT DATA FILE OF PATIENT <br> `C:¥Data¥Sample1.dat` <br> THRESHOLD VALUE OF IONIC INTENSITY: `10` `%` ▼ <br> RETENTION TIME RANGE (min): `20` – `60` <br> RETENTION TIME ACCURACY (sec): `10` <br> MASS RANGE (Da): `50` – `40000` <br> MASS ACCURACY (Da): `1` |
| CONDITIONS FOR ANALYSIS RESULT OUTPUT <br> COMMON MS/MS SPECTRA FILE <br> `C:¥Data¥Common.aaa` <br> MS/MS SPECTRA AND OTHER FILES SPECIFIC TO HEALTHY PERSON <br> `C:¥Data¥Standard.aaa` <br> MS/MS SPECTRA AND OTHER FILES SPECIFIC TO PATIENT <br> `C:¥Data¥Sample1.aaa` |
| [ PRECURSOR ION COMPARATIVE ANALYSIS EXECUTION ] |

Fig. 6

| RETENTION TIME (MIN) | | MEASURED MASS VALUE (MASS/CHARGE) |
| --- | --- | --- |
| APPEARANCE | DISAPPEARANCE | |
| 0.0 | 90.1 | 345.4 |
| 14.2 | 14.5 | 639.6 |
| 14.5 | 15.1 | 570.2 |
| ... | ... | ... |

Fig. 7

| PATTERN | MS¹ SPECTRA OF HEALTHY PERSON | MS² SPECTRA OF HEALTHY PERSON | MS¹ SPECTRA OF PATIENT | MS² SPECTRA OF PATIENT | REMARKS |
|---|---|---|---|---|---|
| A | ○ | ○ | ○ | ○ | (EXCLUDE WHEN PATIENT SAMPLE IS MEASURED) COMMONLY PRESENT, ADOPTING MS/MS SPECTRA OF HEALTHY PERSON, PATIENT OR BOTH |
| B | ○ | ○ | ○ | — | COMMONLY PRESENT, ADOPTING MS/MS SPECTRA OF HEALTHY PERSON |
| C | ○ | ○ | × | — | PRESENT ONLY IN HEALTHY PERSON, ADOPTING MS/MS SPECTRA OF HEALTHY PERSON |
| D | ○ | — | ○ | ○ | COMMONLY PRESENT, ADOPTING MS/MS SPECTRA OF PATIENT |
| E | ○ | — | ○ | — | COMMONLY PRESENT, NO MS/MS SPECTRUM |
| F | ○ | — | × | — | PRESENT ONLY IN HEALTHY PERSON, NO MS/MS SPECTRUM |
| G | × | — | ○ | ○ | PRESENT ONLY IN PATIENT, ADOPTING MS/MS SPECTRA OF PATIENT |
| H | × | — | ○ | — | PRESENT ONLY IN PATIENT, NO MS/MS SPECTRUM |

MASS ANALYSIS METHOD AND MASS ANALYSIS APPARATUS

BACKGROUND OF THE INVENTION

1. Field of the Invention

The present invention relates to a mass analysis method and a mass analysis apparatus for conducting analysis on proteins or peptides in samples by mass analysis.

2. Background Art

Proteins in vivo play a number of roles such as formation of cytoskeleton, muscle contraction, host defense (immunization), signal transduction, various types of catalysis or blood coagulation. However, the specific role of each protein has not been elucidated for many of the proteins.

Thus, while focusing on presence/absence of a particular disease, presence/absence of an administration of a drug, temporal changes of medication, presence/absence or degree of physical stress, and the difference in tissues, attempts have been made to comprehensively detect proteins expressed in vivo and detect the difference of proteins which characterizes them.

For example, if a protein that is expressed in patients suffering from a particular disease but not expressed in healthy persons is found, the protein may be associated with the disease in some way or other. Further, research on functions of the protein may clarify a cause of the disease and enable the development of a drug. Also, since a characteristic to the disease is given, there is a possibility that accurate diagnosis will be available among a group of diseases giving the similar findings.

In this way, it is considered very important to comprehensively identify and comparatively analyze proteins in vivo.

For this purpose, known is a method of analyzing a protein with a mass analysis apparatus. In this analysis method, an ion derived from a peptide molecule is selected as a precursor ion, and fragmented and then, mass spectrum having a structural data of the peptide (that is, MS/MS spectrum or $MS^2$ spectrum) is obtained, which are realized.

In mass analyzing successively components separated by liquid chromatograph, $MS^1$ spectrum (mass spectrum obtained by observing a precursor ion in contrast to $MS^2$ spectrum) includes time series information derived from each component separated by liquid chromatograph. In particular, when a peptide is ionized by ESI (Electrospray Ionization), a proton (hydrogen ion: $H^+$) or the like is added to or eliminated from its molecular ion, which is often observed as a multiply-charged ion.

Further, $MS^2$ spectrum includes structural information regarding a precursor ion. Particularly, in the case of peptide, for example, an ion generated by fragmentation of C—N bond in peptide bond of amino acid is observed, and structural knowledge is often obtained. As long as a precursor ion providing $MS^2$ spectrum is derived from peptide separated by liquid chromatograph, the same precursor ion is ideally observed at the same retention time when the measurement is carried out under the same conditions.

Furthermore, a method is realized wherein a precursor ion is selected from ions observed in $MS^2$ spectrum and fragmented for the obtainment of mass spectrum (that is, $MS^3$ spectrum). In particular, when $MS^2$ spectra are very similar even though ions have different structures, or when the number of types of ions observed in $MS^2$ spectrum is small and structural information is poor, the obtainment of $MS^3$ spectrum is sometimes effective in structure analysis.

Patent Document 1 describes sample evaluation by mass spectrum comparison. In this patent document 1, a standard signal of a fragment of a viral gene transfer vector is prepared, a sample signal is compared with the standard signal, the presence of impurities is detected, and a signal corresponding to an impurity fragment is identified.

[Patent Document 1] JP Patent Publication (Kohyo) No. 2003-510008

However, the above conventional art has the following problems in identifying a protein and peptide in sample.

(a) The Number of Identifications of a Plurality of Components in Sample

In conducting identification with mass spectrum of a precursor ion derived from components in a sample, ions from all components are selected as precursor ions, and it is ideal to obtain mass spectra thereof However, there are restrictions on time during which candidate ions to a precursor ion are observable or measurement time necessary for obtaining MS/MS spectra. Thus, it is not necessarily possible to select ions corresponding to all the existing components as precursor ion and to obtain MS/MS spectra thereof In other words, if ions derived from all the components are selected as precursor ions to obtain mass spectra thereof, it requires very long time. Therefore, it is difficult for practical purpose.

(b) Measurement Time and Sample Amount

As a method to increase the above number of identifications, a method is provided wherein the same sample is measured several times and information regarding more components is obtained. However, repetition of the measurement needs more time, resulting in decreased throughput. Further, an amount of the sample should be enough to conduct several-times measurement, so it is difficult to conduct measurement when the sample availability is low.

(c) Time Necessary for Component Identification

Even when MS/MS spectra are obtained from many kinds of ions, it requires time to analyze corresponding components, so it is not necessarily efficient. In particular, in a method of separating protein or peptide by electrophoresis, electrophoresis itself consumes time.

(d) Identification of Trace Component

In the case of electrophoresis, a certain concentration is required for image identification, and thus less amount of trace component is neglected. Further, in analyzing an enzymatically digested sample by liquid chromatograph, MS/MS spectra derived from trace components having close retention times cannot often be obtained.

In particular, when measurements and analyses are repeated on plural kinds of samples, the above points are more important.

SUMMARY OF THE INVENTION

An object of the present invention is to realize a mass analysis method and apparatus that enable identification of biological samples with high speed and high sensitivity.

In the present invention, a mass spectrum is obtained by ionizing a standard sample, an ion is selected from the mass spectrum as a first precursor ion, and a mass spectrum of the first precursor ion is obtained. Then, a mass spectrum is obtained by ionizing a sample of interest to be measured, an ion is selected as a second precursor ion from the mass spectrum with exclusion of ions common to the first precursor ion, and a mass spectrum of the second precursor ion is obtained.

Next, selected are a mass spectrum of an ion, in the first precursor ion, common to the ion of mass spectrum of the sample of interest to be measured; a mass spectrum of an ion, in the first precursor ion, different to the ion of mass spectrum of the sample of interest to be measured; and a mass spectrum of the second precursor ion. Then, the selected mass spectra are compared with each other, thereby analyzing the component of the sample of interest to be measured.

The present invention does not need to conduct MS/MS on all the precursor ions in mass spectrum obtained from the sample to be measured, and can provide a mass analysis method and apparatus that enable identification of biological samples with high speed and high sensitivity.

The present invention provides higher possibility to identify trace components.

BRIEF DESCRIPTION OF THE DRAWINGS

FIG. 4 is a drawing showing an exemplary screen for preparing a precursor ion exclusion list;

FIG. 5 is a drawing showing an exemplary screen for precursor ion comparative analysis;

FIG. 6 is a drawing showing a list of ranges of retention time and measured mass values (mass/charge); and FIG. 7 is a drawing showing processing patterns in precursor ion comparative analysis.

DETAILED DESCRIPTION OF THE PREFERRED EMBODIMENTS

Figure 1:
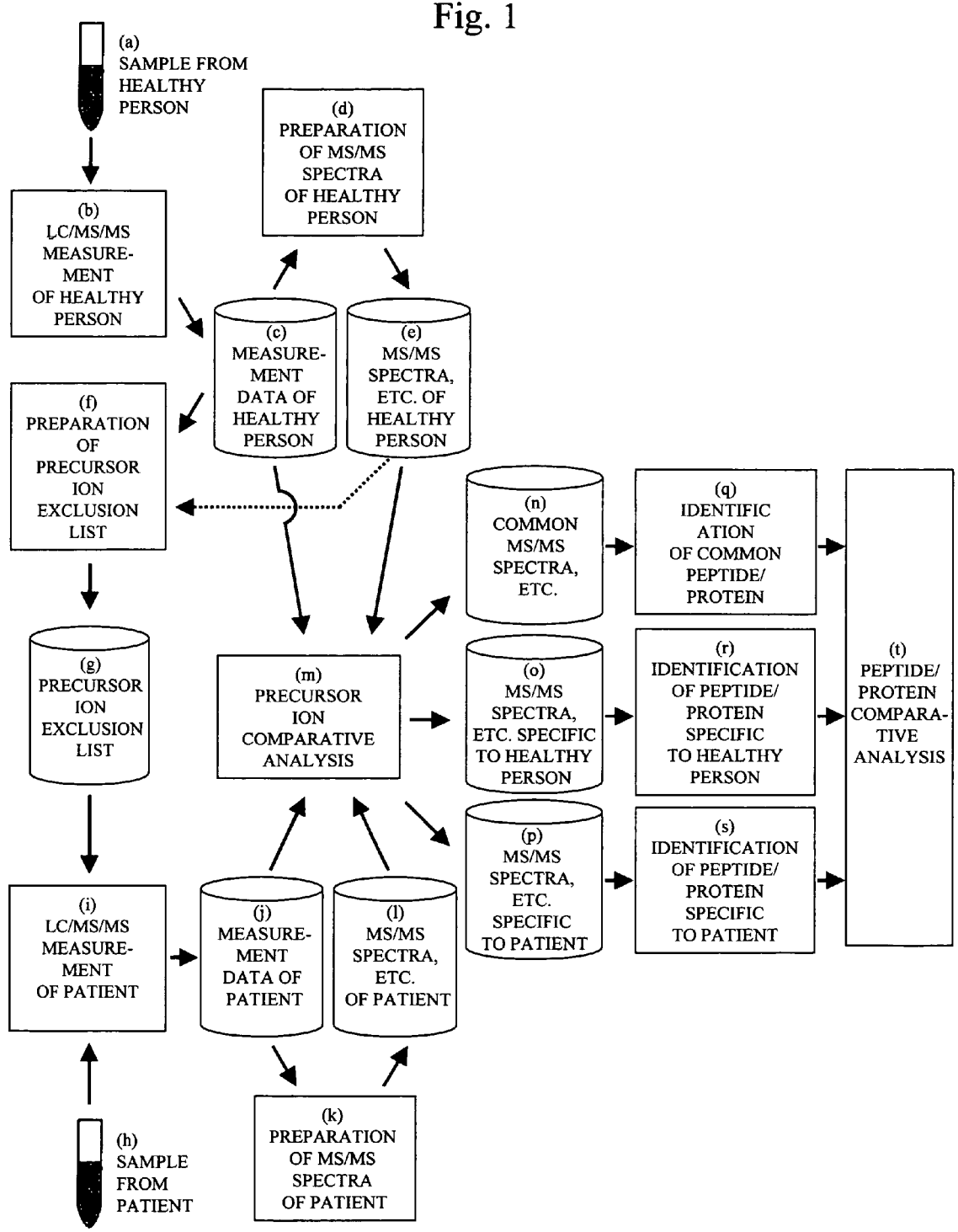
FIG. 1 is a drawing illustrating the operation of a mass analysis apparatus according to an embodiment of the present invention.
Figure 2:
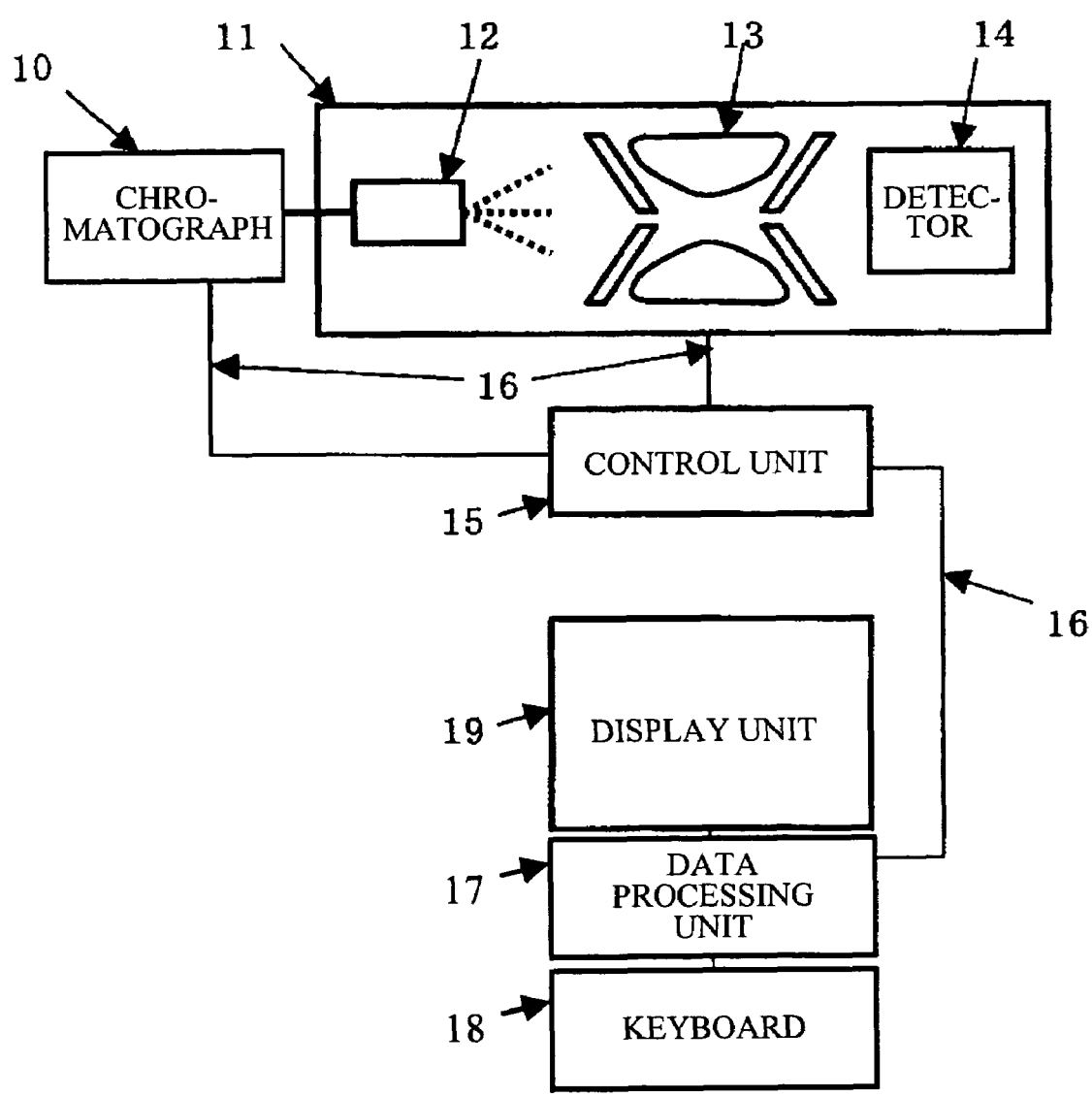
FIG. 2 is a schematic diagram of the mass analysis apparatus according to an embodiment of the present invention.

FIG. 1 is a drawing illustrating the operation of a mass analysis apparatus of an embodiment according to the present invention. FIG. 2 is a schematic diagram of the mass analysis apparatus of an embodiment according to the present invention.

In FIG. 2, the mass analysis apparatus comprises a chromatography apparatus 10 for sample separation, a mass analysis apparatus main body 11, a control unit 15, and a data processing unit 17. The chromatography apparatus 10 and the mass analysis apparatus main body 11 are connected to the control unit 15 with a signal line 16. The control unit 15 and data processing unit 17 are connected to each other with the signal line 16.

The mass analysis apparatus main body 11 comprises an ion source 12 for ionizing a sample, a mass analysis unit 13, and a detection unit 14. Further, the data processing unit 17 is connected to a keyboard 18 and a display unit 19.

The data processing unit 17 is connectable to an external public line, such as the Internet, and thereby it can access a database connected on the Internet to obtain necessary information. Further, information of the database may be obtained by using a recording medium such as CD-ROM.

In addition, an illustrated example includes a chromatography apparatus and an ion trap mass spectrometer, but applicable are all kinds of mass spectrometers that permit $MS^2$ analysis (that is MS/MS analysis) through precursor ion selection by $MS^1$ analysis. Also, a preferable ion source is one that can ionize proteins or peptides with as little as destruction thereof. For example, an Electro Spray Ionization (ESI) is usable. Further, a chromatography apparatus is not necessarily required, and a mass analysis apparatus employing a Matrix Assisted Laser Desorption Ionization (MALDI), etc. is applicable.

Next, the operation of the mass analysis apparatus of the embodiment according to the present invention will be described by referring to FIG. 1. In this embodiment, enzymatically digested proteins derived from a healthy person and a patient are assumed as a standard biological sample and a biological sample to be compared, respectively. However, the combination of samples is not limited thereto, and applicable are drug-administered and not administered specimens, and specimens derived from different tissues such as pancreas and liver, and epithelial cells and dermal cells. Further, when a stable isotope label is used, a mixture specimen thereof may be used as one sample for the present method.

As a basic flow, a sample from a healthy person is analyzed with a tandem mass spectrometer, and MS/MS spectra and a precursor ion exclusion list are prepared. Then, based on the exclusion list, a sample from a patient is analyzed while precursor ions are selected, and then MS/MS spectra of the patient are prepared in the same manner as that of the healthy person. Thereafter, they are comparatively analyzed. The resultant MS/MS spectra are sorted out depending on ions specific to healthy person, ions specific to patient, and ions commonly expressed, and identification and comparative analysis of proteins are conducted.

Hereinafter, detailed explanation will be provided by referring to FIG. 1.

(a) Pre-Treatment of a Sample from a Healthy Person

As a standard sample, a sample from a healthy person is assumed. Blood or urine, or a tissue of an organ, etc. from a healthy person, is collected, and protein extraction or enzymatic digestion, for example, by trypsin is conducted. Such pre-treatment is carried out to permit LC/MS/MS measurements mentioned below.

(b) LC/MS/MS Measurements of a Sample from a Healthy Person

The sample from the healthy person is separated by liquid chromatography, and at the same time sequentially ionized by a method such as electrospray ionization. Further, an $MS^1$ spectrum is measured by a tandem mass analysis apparatus. Ions measured here include ones from peptides, and they are fragmented as precursor ions to obtain an $MS^2$ spectrum.

In this way, an $MS^1$ spectrum and an $MS^2$ spectrum of one or a plurality of ions selected therefrom are alternately obtained.

(c) Storage of Measurement Data for a Healthy Person

Data obtained by measuring the sample from the healthy person with the tandem mass analysis apparatus is stored in storage means. The measurement data include $MS^1$ spectra and $MS^2$ spectra, and retention times at which the spectra are obtained.

(d) Preparation of MS/MS Spectra of Healthy Person

MS/MS spectra, etc. of healthy person are extracted from the measurement data of healthy person. As information necessary for identification of proteins or peptides, and precursor ion comparative analysis described below, MS/MS spectra, and mass, charge, ionic intensity, retention time, and intensity pattern of isotopic ion of corresponding precursor ion are obtained from $MS^1$ spectra, and accumulated.

In this connection, when several MS/MS spectra of precursor ions derived from the identical component are obtained, MS/MS spectra obtained by adding or averaging ionic intensity for those measured values of mass-to-charge ratio are used as integrated one for S/N ratio improvement.

(e) Storage of MS/MS Spectra, etc. of Healthy Person

As MS/MS spectra, etc. of healthy person, MS/MS spectra, and mass, charge, ionic intensity, retention time, and intensity pattern of isotopic ion of corresponding precursor ion are accumulated, and stored in a storage means.

(f) Preparation of Precursor Ion Exclusion List

Information of precursor ions, from which MS/MS spectra are obtained, is extracted from the measurement data of healthy person of the above (c), and a precursor ion exclusion list is prepared. Precursor ion information herein includes retention time, mass, charge, and intensity pattern of isotopic ion.

In this connection, when a range of retention time (initial time-end time) is registered in the precursor ion exclusion list, it is possible to exclude an ion observed for a comparatively long period from other ions. Further, it may be considered that information on apparatus-derived ions other than peptides is added to the list.

As a method to prepare a precursor ion exclusion list, it is considered that a list of precursor ions to be excluded is obtained only from (e) accumulated information such as MS/MS spectra of healthy person.

As further methods, representative values other than ranges of retention times may be registered, and those representative values are times at which ions are detected with maximum ionic intensity, or times at which MS/MS spectra are measured. Furthermore, it is assumed that the control unit of the mass analysis apparatus prepares the precursor ion exclusion list in real time during LC/MS/MS measurement of sample of healthy person.

(g) Storage of Precursor Ion Exclusion List

In the measurement of a sample to be compared, a list of matters to be excluded from precursor ions for the obtainment of MS/MS spectra is stored. FIG. 6 shows an exemplary list of ranges of retention time and measured mass values (mass/charge).

(h) Pre-Treatment of a Sample of a Patient

As a sample to be compared with the sample of the healthy person, a sample from a patient is assumed. This is collected from blood or urine, or a tissue of an organ, etc. of patient in the same manner as the sample of the healthy person, and protein extraction and enzymatic digestion, for example, by trypsin are conducted.

(i) LC/MS/MS Measurement for a Patient

LC/MS/MS measurement for the sample from the patient is also conducted in the same manner as for the sample from the healthy person. In doing so, the same measurement conditions are basically applied so that the spectrum of the same peptide as included in a sample of healthy person appears at as much the same retention time as possible. However, a matter prescribed in the precursor ion exclusion list prepared in above-mentioned process (g) is excluded from precursor ion candidates for the obtainment of MS/MS spectra thereof By doing so, ions of peptide only present in the patient sample are ideally selected as precursor ions, and MS/MS spectra thereof can be obtained.

In applying the exclusion list, a likelihood for retention time is provided. For example, it is preferable that a user can properly set an allowable error of ±20 seconds or 5%, etc. to retention time designated in the precursor ion exclusion list.

When a range of retention time is designated in the precursor ion exclusion list, values with likelihood may be set in advance.

(j) Storage of Measurement Data of Patients

It is assumed that measurement data of patient is registered in the same format as the measurement data of healthy person. In other words, it includes $MS^1$, and $MS^2$ spectra obtained with a tandem mass analysis apparatus, and retention times at which they are obtained.

When an ion not present in the precursor ion exclusion list is selected in the process (i) LC/MS/MS measurement of patient and the measurement data of patient is compared with the measurement data of healthy person, the data include MS/MS spectra of precursor ion derived from a newly measured component. Also, when an ion that is not selected due to low ionic intensity in the measurement of healthy person, is selected as a precursor ion, there is a possibility that $MS^2$ spectra is obtained.

(k) Preparation of MS/MS Spectra of Patients

MS/MS spectra of patient are prepared in the same manner as in MS/MS spectra of healthy person. That is, as MS/MS spectra, etc. of patient, MS/MS spectra, and mass, charge, ionic intensity, retention time, and intensity pattern of isotopic ion of corresponding precursor ion are obtained from $MS^1$ spectra, and accumulated.

(l) Storage of MS/MS Spectra, etc. of Patients

As MS/MS spectra, etc. of patient, MS/MS spectra, and mass, charge, ionic intensity, retention time, and intensity pattern of isotopic ion of corresponding precursor ion are accumulated, and stored in a storage means in the same manner as MS/MS spectra of healthy person.

(m) Precursor Ion Comparative Analysis

Precursor ion comparative analysis performs: storage of common MS/MS spectra, etc. of healthy person and patient (n); storage of MS/MS spectra, etc. specific to healthy person (o); and storage of MS/MS spectra, etc. specific to patient (p), by referring to the measurement data of healthy person in process (c); MS/MS spectra, etc. of healthy person in process (e); the measurement data of patient in process (j); and MS/MS spectra, etc. of patient in process (I), all of which are stored.

The MS/MS spectra, etc. of healthy person in process (e) and MS/MS spectra, etc. of patient in process (1) are generated based on the measurement data of healthy person stored in process (c) and the measurement data of patient stored in process (j), respectively.

Therefore, precursor ion comparative analysis (m) can be carried out by referring to at least the measurement data of healthy person stored in process (c) and the measurement data of patient stored in process (j).

Detailed explanation on precursor ion comparative analysis in the above (m) will be provided below.

(n) Storage of Common MS/MS Spectra, etc.

MS/MS spectra that are generated in the above (m) precursor ion comparative analysis and derived from precursor ions that are determined to be common to healthy person and patient, and mass, charge, ionic intensity, and retention time of corresponding precursor ion are accumulated and stored. Regarding the ionic intensity of the corresponding precursor ion, the measured values of healthy person and patient both are included, and thereby comparison on ionic intensity is available later.

(o) Storage of MS/MS Spectra, etc. Specific to Healthy Person

MS/MS spectra that are generated in the above (m) precursor ion comparative analysis and derived from precursor ions that are determined to be present only in healthy person, and mass, charge, ionic intensity, and retention time of corresponding precursor ion are accumulated and stored.

(p) Storage of MS/MS Spectra, etc. Specific to Patient

MS/MS spectra that are generated in the above (m) precursor ion comparative analysis and derived from precursor ions that are determined to be present only in patient, and mass, charge, ionic intensity, and retention time of corresponding precursor ion are accumulated and stored.

(q) Identification of Common Peptide/Protein

Based on common MS/MS spectra, etc. stored in the above process (n), corresponding peptide or protein is identified.

(r) Identification of Peptide/Protein Specific to Healthy Person

Based on the MS/MS spectra, etc. specific to healthy person stored in the above process (o), corresponding peptide or protein is identified.

(s) Identification of Peptide/Protein Specific to Patient

Based on the MS/MS spectra, etc. specific to patient stored in the above process (p), corresponding peptide or protein is identified.

(t) Peptide/Protein Comparative Analysis

Identification, etc. of peptide or protein specific to healthy person or patient are carried out, based on the common peptide/protein identified in the above process (q), the healthy person specific peptide/protein identified in the above process (r), and the patient specific peptide/protein identified in the above process (s). Further, it is possible to review quantitative fluctuations through comparison of ionic intensity of precursor ions. In other words, regarding peptide/protein specific to a particular patient, when there are results previously analyzed, it is possible to determine what is increased or decreased by comparing the previous results with the present analysis results.

Described above is a series of operations of mass analysis apparatus, which is one embodiment of the present invention.

Here, correspondency between apparatus configuration shown in FIG. 2 and processing contents shown in FIG. 1 is described. In the LC/MS/MS measurement of healthy person (b) in FIG. 1, selection, etc. of a precursor ion is conducted by the control unit 15. The LC/MS/MS measurement of patient (i) is performed by referring to the precursor ion exclusion list, and that measurement is also conducted by the control unit 15. Information processing related processes other than measurement are conducted by the processing unit 17.

It should be noted that preparation of the precursor ion exclusion list can be conducted by the control unit 15.

Further, the data processing unit 17 is connectable to an external public line such as the Internet. In the above identifying processes (q), (r), and (s), the unit can obtain protein information via the Internet and conduct the identification based on the obtained information.

Next, the precursor ion comparative analysis in the above process (m) will be described in detail.

Figure 3:
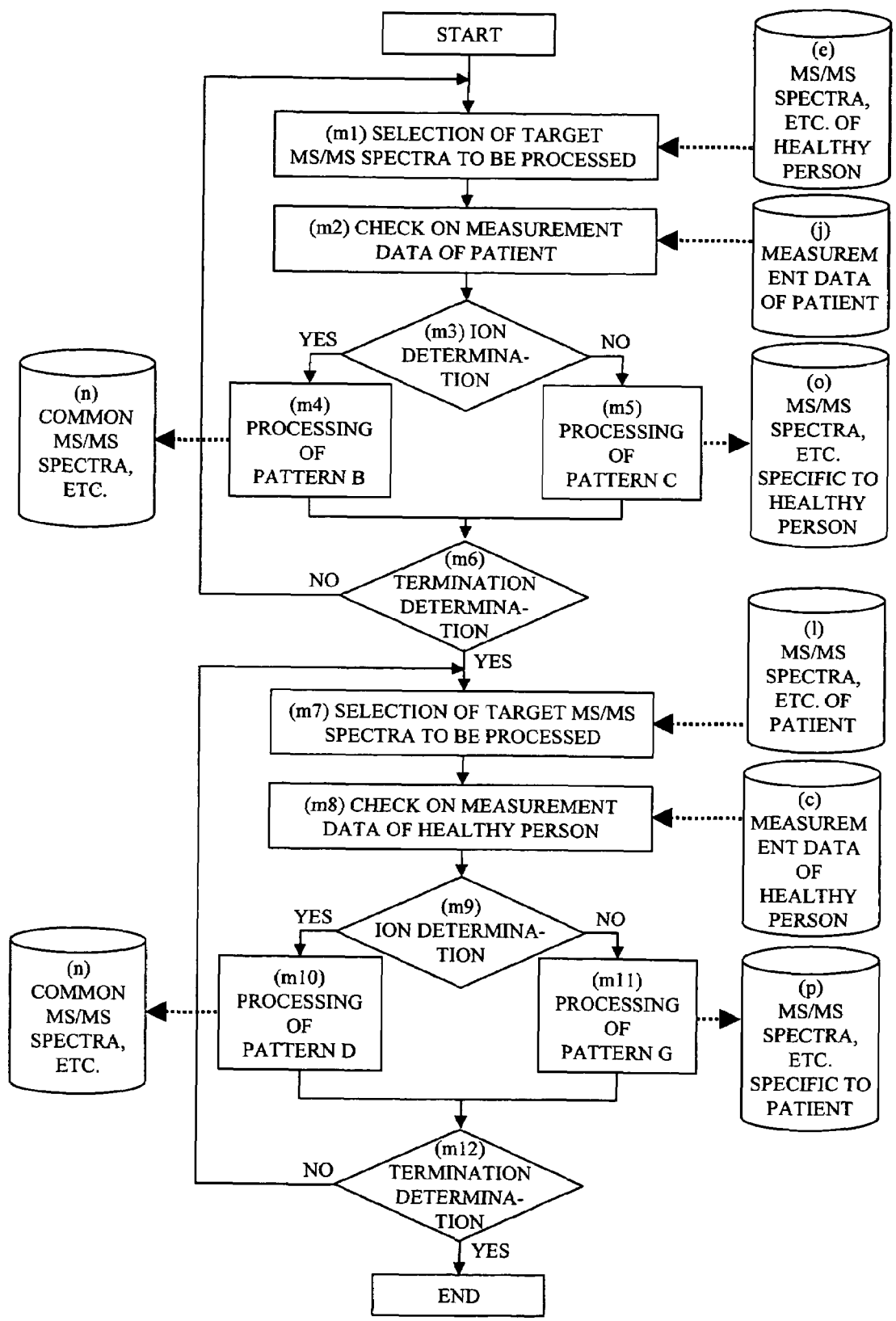
FIG. 3 is an operation flow chart of precursor ion comparative analysis according to an embodiment of the present invention.

FIG. 3 is an operation flow chart of (m) precursor ion comparative analysis. In addition, FIG. 7 is a table showing all cases regarding whether or not an ion derived from the identical component is observed in $MS^1$ spectra of healthy person and patient; and whether or not $MS^2$ spectra are obtained after such ion is selected as a precursor ion.

The "circle" mark in $MS^1$ spectra columns of FIG. 7 indicates that ions are observed in corresponding mass spectra. Further, the "circle" mark in $MS^2$ spectra columns indicates that the ion is selected as a precursor ion and $MS^2$ spectra thereof are obtained.

Hereinafter, explanation will be provided by referring to FIG. 3.

(m1) Selection of Target MS/MS Spectra to be Processed

From MS/MS spectra, etc. of healthy person, MS/MS spectra, and information such as mass, charge, ionic intensity, and retention time of corresponding precursor ion are read-out.

(m2) Check on Measurement Data of Patient

The information on precursor ion read-out in the above process (m1) is checked against the measurement data of patient, and it is evaluated whether an ion corresponding to retention time, mass and the like is present or not.

(m3) Ion Determination

Based on the evaluation results of the above process (m2), it is determined whether an ion corresponding to MS/MS spectra of healthy person is present in $MS^1$ spectra in the measurement data of patient.

(m4) Processing of Pattern B

When an ion corresponding to healthy person and patient in the above (m3) ion determination, Pattern B process of FIG. 7 is conducted. That is, MS/MS spectra, etc. of healthy person are added to common MS/MS spectra, etc.

(m5) Processing of Pattern C

When MS/MS spectrum detected in the healthy person's sample is not present in the patient's sample in the above (m3) ion determination, Pattern C process of FIG. 7 is conducted. That is, MS/MS spectra, etc. of healthy person are added to healthy person specific MS/MS spectra, etc.

(m6) Termination Determination

When all MS/MS spectra, etc. of healthy person are processed, the process (m7) described below is conducted. When there are spectra, etc. that are not processed, turn back to the process (m1) and continue the processing.

(m7) Selection of Target MS/MS Spectra to be Processed

From MS/MS spectra, etc. of patient, MS/MS spectra, and information such as mass, charge, ionic intensity, and retention time of corresponding precursor ion are read-out.

(m8) Check on the Measurement Data of Healthy Person

The information on precursor ion read-out in the above process (m7) is checked against the measurement data of healthy person, and it is evaluated whether an ion corresponding to retention time, mass and the like is present or not.

(m9) Ion Determination

Based on the evaluation results of the above process (m8), it is determined whether an ion corresponding to MS/MS spectra of patient is present in $MS^1$ spectra in the measurement data of healthy person.

(m10) Processing of Pattern D

When an ion corresponding to healthy person and patient in the above (m9) ion determination, Pattern D process of FIG. 7 is conducted. That is, MS/MS spectra, etc. of patient are added to common MS/MS spectra, etc.

(m11) Processing of Pattern G

When MS/MS spectrum detected in the patient's sample is not present in the healthy person's sample in the above (m9) ion determination, Pattern G process of FIG. 7 is conducted. That is, MS/MS spectra, etc. of patient are added to patient specific MS/MS spectra, etc.

(m12) Termination Determination

When the processing of all MS/MS spectra, etc. of patient are finished, the processing is terminated. When there are spectra, etc. that are not processed, turn back to the process (m7) and continue the processing.

In Patterns E, F and H of FIG. 7, no $MS^2$ spectrum is obtained, and therefore, they are neglected since they are not considered to contribute to the identification of peptide or protein.

Further, in Pattern A of FIG. 7, LC/MS/MS measurement of patient is conducted in accordance with precursor ion exclusion list. This pattern is impossible, so this is also neglected.

However, in the case that LC/MS/MS measurement of patient clearly shows higher intensity of ion than that of healthy person, it is considered that MS/MS spectrum of ion, which has already been measured for healthy person, may be obtained for a sample of patient. In such case, MS/MS spectrum with higher intensity of precursor ion is registered in common MS/MS spectra, etc. Otherwise, spectra may be added or averaged and then registration process may be conducted.

Next, a screen for preparation of precursor ion exclusion list to be displayed on the display unit 19 will be described.

FIG. 4 is a drawing showing an exemplary screen for specifying conditions to prepare a precursor ion exclusion list.

In FIG. 4, the conditions to prepare a precursor ion exclusion list are roughly divided into: upper part, analysis conditions on the measurement data of healthy person; middle part, the observed ions in $MS^1$ spectra of the measurement data; and lower part, conditions for outputting the precursor ion exclusion list.

As the analysis conditions on the measurement data of healthy person, measurement data file, threshold value of ionic intensity, retention time range, retention time accuracy, mass range, and mass accuracy are designated. The threshold value of ionic intensity is designated to exclude fine ions, as precursor ions to be registered in an exclusion list of FIG. 1 (g), and % value of mass spectrum or observed value of ion is specified.

Further, ranges of retention time or mass to be registered in the above exclusion list, and time accuracy and mass accuracy for determining that a plurality of ions are identical, are set. In this example, measurement data analysis execution button 20 is specified, and thereby analysis is conducted under the designated conditions. Results thereof are displayed in a list of the observed ions in $MS^1$ spectra of the measurement data.

Furthermore, as the conditions for outputting, multiply-charged ion extension, retention time type, precursor ion exclusion list file, etc. are specified. Here, the multiply-charged ion extension means to specify whether or not each multiply-charged ion of observed ion is to be added to the list. Further, when range is specified for retention time type, the retention time data in the precursor ion exclusion list, a range of retention time at which individual precursor ion is observed, includes that is, retention times both for appearance and disappearance.

When representative value for retention time is specified, a retention time at which a maximum value is given is recorded as the representative value of the ion. Finally, by specifying a precursor ion exclusion list preparation execution button, the analysis results of measurement data are outputted as a specified precursor ion exclusion list file.

Next, described is a screen for precursor ion comparative analysis to be displayed on the display unit 19.

FIG. 5 is a drawing showing an exemplary screen for specifying conditions for precursor ion comparative analysis.

The conditions for precursor ion comparative analysis are roughly divided into: conditions for measurement data comparative analysis; and conditions for analysis result output. As the conditions for measurement data comparative analysis, measurement data file of healthy person and patient, threshold value of ionic intensity, range of retention time or mass, and accuracy of retention time or mass are specified.

The threshold value of ionic intensity is designated to exclude fine ions, as precursor ions to be registered in an exclusion list, and % value of mass spectrum or observed value of ion is designated. Further, ranges of retention time and mass to be registered in the above exclusion list, and time accuracy and mass accuracy for determining that a plurality of ions are identical, are set.

In addition, as the conditions for analysis result output, each MS/MS spectrum file is designated.

Finally, by designating a precursor ion comparative analysis execution button, comparative analysis and file output are executed.

As described above, according to the present invention, mass spectra of a standard sample are obtained, an ion selected from the mass spectra is regarded as a precursor ion, and mass spectra of the precursor ion are obtained. Then, mass spectra of a sample of interest to be measured are obtained, an ion that is newly observed and other than precursor ions measured in the standard sample is selected from the mass spectra of the sample as a precursor ion, and mass spectra thereof are obtained.

Then, identification on peptide/protein specific to standard sample, identification on peptide/protein specific to a sample of interest to be measured, and identification on common peptide/protein of standard sample and the sample of interest are carried out. Based on these identification results, comparative analysis on peptide/protein of the sample of interest to be measured is carried out.

Therefore, without regarding ions derived from all components of the sample of interest to be measured as precursor ions, it is possible to obtain MS/MS spectra, and identify a plurality of components of the sample of interest for a short period and with high sensitivity.

The present invention can be applied to not only separation of sample components by liquid chromatography but also separation of sample components by gas chromatography. When components are separated by gas chromatography, it is preferably applied to analysis of metabolites of biological samples.

Further, the present invention allows effective capture of protein or peptide specifically expressed in a particular disease, and thereby can be applied to search for protein or peptide that is a disease marker.

Though analysis on components is carried out using $MS^1$ spectra and $MS^2$ spectra in the above example, component analysis can be carried out by obtaining $MS^3$ spectra or upper level such as $MS^n$ spectra. Here, $MS^n$ spectra means carrying out MS n times.

Furthermore, isotopic ions in the obtained spectra or ions derived from a background of the mass analysis apparatus are determined, and they can be excluded from precursor ions for a subject matter to be measured. In other words, isotopic ions in the obtained spectra or ions derived from a background of the mass analysis apparatus are added to the precursor ion exclusion list (g) of FIG. 1, and they can be excluded from precursor ions for a subject matter to be measured.

In addition, selection of a precursor ion from the mass spectra obtained for a standard sample is carried out several times. Whenever a precursor ion is selected, a precursor ion for a sample of interest to be measured is determined and mass spectra thereof are obtained. Mass spectra of ion common to ion of mass spectra of the sample of interest and mass spectra of ion different from ion of mass spectra of the sample of interest are obtained, allowing analysis on components of the sample of interest to be measured.

What is claimed is:

1. A mass analysis method for analyzing components of a sample by ionizing and mass-analyzing the sample:
  obtaining a mass spectrum by ionizing a standard sample, selecting an ion from the obtained mass spectrum as a first precursor ion, and obtaining a mass spectrum of the first precursor ion;
  obtaining a mass spectrum by ionizing a sample of interest to be measured, selecting an ion from the obtained mass spectrum as a second precursor ion with exclusion of an ion common to the first precursor ion, and obtaining a mass spectrum of the second precursor ion;
  selecting: a mass spectrum of an ion, in the first precursor ion, common to the ion of mass spectrum of the sample of interest to be measured; a mass spectrum of an ion, in the first precursor ion, different to the ion of mass spectrum of the sample of interest to be measured; and a mass spectrum of the second precursor ion; and
  comparing the selected mass spectra with each other, thereby analyzing the component of the sample of interest to be measured.

2. The mass analysis method according to claim 1, wherein the sample components are separated by liquid chromatography or gas chromatography, the separated components are ionized, and the components of the sample of interest to be measured are analyzed based on mass and retention time of the ion, or mass, retention time, charge, and intensity pattern of isotopic ion of the ion.

3. The mass analysis method according to claim 1, comprising:
  conducting plural times of precursor ion selections from the obtained mass spectrum for the standard sample;
  determining, whenever a precursor ion is selected, the precursor ion of the sample of interest to be measured to obtain mass spectrum;
  obtaining: a mass spectrum of an ion, in the first precursor ion, common to the ion of mass spectrum of the sample of interest to be measured; a mass spectrum of an ion, in the first precursor ion, different to the ion of mass spectrum of the sample of interest to be measured; and a mass spectrum of the second precursor ion.

4. The mass analysis method according to claim 1, wherein, based on ionic intensity of each mass spectrum obtained, an amount of each component in the sample of interest to be measured is analyzed.

5. The mass analysis method according to claim 1, wherein an ion is selected as the second precursor ion with exclusion of an isotopic ion of an ion common to the first precursor ion and an ion derived from a background of a mass analysis apparatus.

6. The mass analysis method according to claims 1, comprising:
  selecting a third precursor ion from the first precursor ion mass spectrum and obtaining a third precursor ion mass spectrum,
  selecting a fourth precursor ion from the second precursor ion mass spectrum and obtaining a fourth precursor ion mass spectrum,
  comparing the standard sample and the sample of interest to be measured with each other in terms of the third and fourth precursor ion mass spectra with each other, thereby analyzing the component of the sample of interest to be measured.

7. The mass analysis method according to claim 6, comprising:
  selecting the fifth or subsequent precursor ion and obtaining an ion mass spectrum thereof; and
  comparing the standard sample and the sample of interest to be measured with each other, thereby analyzing the component of the sample of interest to be measured.

8. A mass analysis method for analyzing a protein and a peptide as components of a sample by ionizing and mass-analyzing the sample:
  obtaining a mass spectrum by ionizing a standard sample, selecting an ion from the obtained mass spectrum as a first precursor ion, obtaining a mass spectrum of the first precursor ion, and preparing a list of a first precursor ion;
  obtaining a mass spectrum by ionizing a sample of interest to be measured, selecting an ion from the obtained mass spectrum as a second precursor ion with exclusion of an ion common to the first precursor ion based on the list of the first precursor ion, and obtaining a mass spectrum of the second precursor ion;
  selecting: a mass spectrum of an ion, in the first precursor ion, common to the ion of mass spectrum of the sample of interest to be measured; a mass spectrum of an ion, in the first precursor ion, different to the ion of mass spectrum of the sample of interest to be measured; and a mass spectrum of the second precursor ion; and
  comparing the selected mass spectra with each other, thereby analyzing the protein and peptide as the component of the sample of interest to be measured.

9. A mass analysis apparatus comprising:
  sample separation means for separating components of a sample;
  ionization means for ionizing the components separated by the sample separation means;
  mass analysis means for mass-analyzing the components ionized by the ionization means; and
  control means for controlling the operation of the ionization means, selecting an ion to be analyzed by the mass analysis means, and controlling the mass analysis means to conduct $MS^n$ analysis,
  wherein the control means allows:
  obtaining a mass spectrum by ionizing a standard sample, selecting an ion from the obtained mass spectrum as a first precursor ion, and obtaining a mass spectrum of the first precursor ion;
  obtaining a mass spectrum by ionizing a sample of interest to be measured, selecting an ion from the obtained mass spectrum as a second precursor ion with exclusion of an ion common to the first precursor ion, and obtaining a mass spectrum of the second precursor ion;
  selecting: a mass spectrum of an ion, in the first precursor ion, common to the ion of mass spectrum of the sample of interest to be measured; a mass spectrum of an ion, in the first precursor ion, different to the ion of mass spectrum of the sample of interest to be measured; and a mass spectrum of the second precursor ion; and
  comparing the selected mass spectra with each other, thereby analyzing the component of the sample of interest to be measured.

10. The mass analysis apparatus according to claim 9, wherein:
  the sample separation means is liquid chromatograph or gas chromatograph; and
  the control means allows the sample component separated by the sample separation means to be ionized, and analyzing the components of the sample of interest to be measured based on mass, retention time of the ion, or mass, retention time, charge, intensity pattern of isotopic ion of the ion.

11. The mass analysis apparatus according to claim 9, wherein the control means allows:

conducting plural times of precursor ion selections from the obtained mass spectrum for the standard sample;

determining the precursor ion of the sample to be measured to obtain mass spectrum whenever a precursor ion is selected; and extracting: a mass spectrum of an ion, in the first precursor ion, common to the ion of mass spectrum of the sample of interest to be measured; a mass spectrum of an ion, in the first precursor ion, different to the ion of mass spectrum of the sample of interest to be measured; and a mass spectrum of the second precursor ion.

12. The mass analysis apparatus according to claim 9, wherein, based on ionic intensity of each mass spectrum obtained, an amount of each component in the sample of interest to be measured is analyzed.

* * * * *